United States Patent
Aamir et al.

(10) Patent No.: US 11,866,755 B1
(45) Date of Patent: Jan. 9, 2024

(54) FERROUS PEBBLES AS A CATALYST FOR ENHANCED METHANE GENERATION FROM RICE HUSK

(71) Applicant: KING FAISAL UNIVERSITY, Al-Ahsa (SA)

(72) Inventors: Muhammad Aamir, Al-Ahsa (SA); Muhammad Hassan, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/237,027

(22) Filed: Aug. 23, 2023

(51) Int. Cl.
*C12P 5/02* (2006.01)
*C12M 1/107* (2006.01)

(52) U.S. Cl.
CPC ............. *C12P 5/023* (2013.01); *C12M 21/04* (2013.01)

(58) Field of Classification Search
None
See application file for complete search history.

(56) References Cited

U.S. PATENT DOCUMENTS

2011/0008865 A1    1/2011    Lee

OTHER PUBLICATIONS

Fuqing Xu, et al., "Anaerobic digestion of food waste—Challenges and opportunities", Bioresource Technology, vol. 247, pp. 1-39, First available online Sep. 11, 2017.
Nguyen Vo Chau Ngan, et al., "Anaerobic Digestion of Rice Straw for Biogas Production", Sustainable Rice Straw Management, pp. 65-92, First available online Nov. 28, 2019.
Yue Xu, et al., "Effect of Iron Supplementation on the Biogas Production and Microbial Community Distribution During Anaerobic Digestion of Food Waste Process", Research Square, pp. 1-18, First available online Jul. 6, 2021.

*Primary Examiner* — Robert J Yamasaki
(74) *Attorney, Agent, or Firm* — Nath, Goldberg & Meyer; Richard C. Litman

(57) ABSTRACT

A method and system for enhancing methane generation in biogas production includes feeding cow manure and glucose into a semi-continuous stirring tank reactor. Incubating the cow manure and glucose to form waste activated sludge with methanogen growth. The methanogen growth is enhanced by surface areas of ferrous pebbles within the semi-continuous stirring tank reactor. Feeding rice husk and water into the semi-continuous stirring tank reactor. Mixing the rice husk, the water, and the formed waste activated sludge together to form a mixture. Initiating an anaerobic digestion process during the mixing to produce high volatile fatty acids. Increasing the production of the high volatile fatty acids to a higher level by enhancing adsorption of the methanogen microorganisms onto the ferrous pebbles. Reacting the higher level of the high volatile fatty acids with the ferrous pebbles to increase conversion of the higher level of volatile fatty acids to methane while producing biogas.

20 Claims, 1 Drawing Sheet

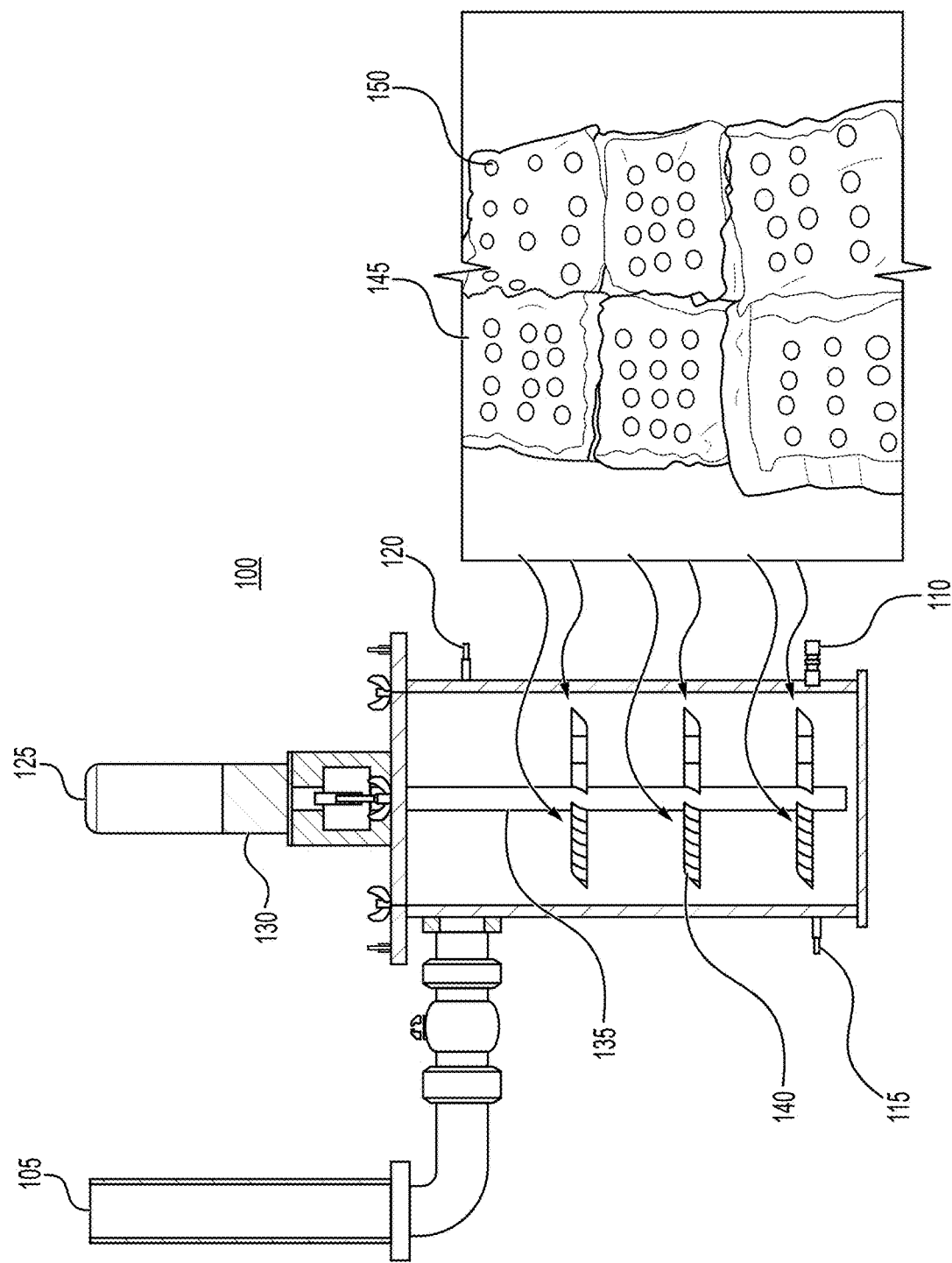

FERROUS PEBBLES AS A CATALYST FOR ENHANCED METHANE GENERATION FROM RICE HUSK

FIELD AND BACKGROUND

The disclosure of the present patent application relates to a method, and particularly to a method and system for enhancing methane generation in biogas production.

DESCRIPTION OF THE PRIOR ART

Methane is a colorless and odorless flammable gas. It is an important fuel source and major component of natural gas. Methane is used for a variety of different purposes including heating, cooking, fuel for powering internal combustion engines, manufacturing of organic chemicals, and generation of electricity.

Despite its benefits, methane has several drawbacks. It is the second most abundant
greenhouse gas, after carbon dioxide. Methane trap about 80 time more heat than carbon dioxide, making it a major contributor to climate change. When methane is emitted into the environment, it stays in the atmosphere and affects the Earth's climate. Extraction of fossil fuels, such as oil, gas, and coal, is the largest source of methane emission.

As concerns of global warming intensify, there is increased pressure to reduce the amount of greenhouse gas released into the atmosphere. There is also growing demand for curbing dependence on fossil fuels as a main source for methane gas due to dwindling supply of fossil fuels worldwide.

One suggested method for solving these problems is to use biogas. There are many advantages to biogas. For one, biogas is a form of green and sustainable energy. Production of biogas lowers methane emissions by capturing methane gas and using it as fuel. Energy is not required for biogas generation since the process for producing gas is natural. Raw materials for biogas production such as animal manure, food wastes, and crop residues, are renewable and highly sustainable.

Biogas can typically consist of methane, carbon dioxide, a small amount of hydrogen sulfide, and moisture. It can be produced by an anaerobic digestion process where organic matter is decomposed in the presence of bacteria or microorganism in an oxygen-free environment. The four successive stages of the anaerobic digestion process are hydrolysis, acidogenesis, acetogenesis and methanogenesis. The anaerobic digestion process takes place in a biogas reactor or digester.

While methane content in biogas typically ranges from 45%-75% by volume, there is a need to enhance methane generation during the anaerobic digestion process.

SUMMARY

The present subject matter relates to a method of enhancing methane generation in biogas production which, in one embodiment, includes installing a plurality of porous linen pouches onto a plurality of stirrer blades of a semi-continuous stirring tank reactor. Each of the plurality of porous linen pouches have a plurality of ferrous pebbles. Cow manure and glucose can be fed into the semi-continuous stirring tank reactor via a feedstock inlet. Incubating the cow manure and glucose inside the semi-continuous stirring tank reactor for a duration of time can form waste activated sludge with methanogen growth. The methanogen growth can be enhanced by surface areas of each of the plurality of ferrous pebbles. Flowing heated water through a water jacket inlet and a water jacket outlet surrounding an exterior of the semi-continuous stirring tank reactor can heat the semi-continuous stirring tank reactor to provide a mesophilic condition. Rice husk and water can be fed into the semi-continuous stirring tank reactor via the feedstock inlet. Mixing the rice husk, the water, and the formed waste activated sludge together can form a mixture. A pH of the mixture can be between about 6.5 and about 7.5. An anaerobic digestion process can be initiated during the mixing. The anaerobic digestion process can include hydrolysis, acidogenesis, acetogenesis, and/or methanogenesis to produce high volatile fatty acids. Increasing the production of the high volatile fatty acids to a higher level can be achieved by enhancing adsorption of the methanogen microorganisms onto the surface areas of each of the plurality of ferrous pebbles. Reacting the higher level of the high volatile fatty acids with each of the plurality of ferrous pebbles can increase conversion of the higher level of volatile fatty acids to methane while producing biogas.

In an embodiment, each of the plurality of ferrous pebbles ca be stitched within a respective one of each of the plurality of porous linen pouches. Further, each of the plurality of ferrous pebbles can have a circular shape.

In another embodiment, the plurality of stirrer blades can include 6 stirrer blades and the plurality of porous linen pouches can include 6 porous linen pouches.

In a further embodiment, each of the plurality of ferrous pebbles in each of the plurality of porous linen pouches can include 12 ferrous pebbles.

In an embodiment, one of each of the plurality of porous linen pouches can be installed on one of each of the plurality of stirrer blades.

In some embodiments, the plurality of ferrous pebbles can include 72 total ferrous pebbles having a total exposed surface area of 241.63 $cm^2$, and a dimension of each of the plurality of ferrous pebbles can include a diameter of 9.5 mm and a height of 6.5 mm.

In some embodiments, a total volume of the waste activated sludge, rice husk, and water within the semi-continuous stirring tank reactor can be 10 L and a total weight of the plurality of ferrous pebbles can be 300 grams.

In some embodiments, a total of the plurality of ferrous pebbles applied to the semi-continuous stirring tank reactor can be 30 g/L.

In some embodiments, the glucose can be fed continuously to the semi-continuous stirring tank reactor at a rate of 2 grams per liter per day.

In some embodiments, the duration of time can be 15 days.

In some embodiments, the rice husk can be fed to the semi-continuous stirring tank reactor at a rate of 5 grams of volatile solid per liter per day.

In some embodiments, a pH of the waste activated sludge and the water in the semi-continuous stirring tank reactor can be about 6.9 and about 7 respectively.

The mesophilic condition can include heating the semi-continuous stirring tank reactor to about 37±1° C. in some embodiments.

The heated water flowing through the water jacket inlet and water jacket outlet can have a temperature of about 37±1° C. in some embodiments.

The mixing can be provided by the stirrer blades being rotated automatically at a speed of 360 rpm for 5 minutes every hour for 180 days in some embodiments.

The methanogen microorganisms from the waste activated sludge can be reacted with the rice husk to produce the high volatile fatty acids during the acidogenesis and acetogenesis processes in some embodiments.

In further embodiments, the present subject matter relates to a system for enhancing methane generation in biogas production, the system including: a semi-continuous stirring tank reactor having a feedstock inlet, a feedstock outlet, a water jacket inlet, a water jacket outlet, a motor, a gear box, a stirrer, a plurality of stirrer blades, and a plurality of porous linen pouches having a plurality of ferrous pebbles disposed therein, one of each of the plurality of porous linen pouches attached to one of each of the plurality of stirrer blades; the semi-continuous stirring tank reactor receives and incubate cow manure and glucose to form waste activated sludge with methanogen growth; the feedstock inlet feeds rice husk and water to the semi-continuous stirring tank reactor; the feedstock outlet discharges rice husk, water, and waste activated sludge from the semi-continuous stirring tank reactor; the water jacket inlet and water jacket outlet accepts flowing water to heat the semi-continuous stirring tank reactor to a mesophilic condition; the motor is connected to the gearbox, stirrer, and the plurality of stirrer blades; and the motor is connected to an Arduino circuit which operate the motor.

In an embodiment, the motor can automatically rotate the plurality of stirrer blades at a speed of 360 rpm for 5 minutes every hour for 180 days to mix the rice husk, water, and the waste activated sludge together to form a mixture.

In certain embodiments, the plurality of stirrer blades can include 6 stirrer blades and the plurality of porous linen pouches can include 6 porous linen pouches, the plurality of ferrous pebbles can include 72 total ferrous pebbles having a total exposed surface area of 241.63 $cm^2$, and a dimension of each of the plurality of ferrous pebbles can include a diameter of 9.5 mm and a height of 6.5 mm.

In another embodiment, each of the plurality of ferrous pebbles in each of the plurality of porous linen pouches can include 12 ferrous pebbles.

These and other features of the present subject matter will become readily apparent upon further review of the following specification.

BRIEF DESCRIPTION OF DRAWINGS

FIG. 1 is an illustration of a system for enhancing methane generation in biogas production.

Similar reference characters denote corresponding features consistently throughout the attached drawings.

DETAILED DESCRIPTION

The following definitions are provided for the purpose of understanding the present subject matter and for construing the appended patent claims.

Definitions

Throughout the application, where compositions or systems are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a system or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a method for enhancing methane generation in biogas production.

FIG. 1 is an illustration of a system for enhancing methane generation in biogas production. It includes a semi-continuous stirring tank reactor 100 comprising a feedstock inlet 105, a feedstock outlet 110, a water jacket inlet 115, a water jacket outlet 120, a motor 125, a gear box 130, a stirrer 135, a plurality of stirrer blades 140, and a plurality of porous linen pouches 145 having a plurality of ferrous pebbles 150 disposed therein, one of each of the plurality of porous linen pouches 145 attached to one of each of the plurality of stirrer blades 140. The plurality of stirrer blades 140 includes 6 stirrer blades and the plurality of porous linen pouches 145 includes 6 porous linen pouches. Each of the plurality of ferrous pebbles 150 in each of the plurality of porous linen pouches 145 includes 12 ferrous pebbles. Therefore, each porous linen pouch 145 contains 12 ferrous pebbles 145 and each of the 6 stirrer blades 140 have a porous linen pouch 145 attached thereon. Each of the plurality of ferrous pebbles 150 are stitched within a respective one of each of the plurality of porous linen pouches 145 and each of the plurality of ferrous pebbles 150 have a circular shape.

The plurality of ferrous pebbles 150 includes 72 total ferrous pebbles having a total exposed surface area of 241.63 $cm^2$, and a dimension of each of the plurality of ferrous pebbles 150 includes a diameter of 9.5 mm and a height of 6.5 mm. The plurality of ferrous pebbles 150 provides a high adsorption surface area to help methanogen microorganisms to grow within the semi-continuous stirring tank reactor 100 during an incubation period, for oxidation, and for allowing more methanogens microorganisms during an anaerobic digestion process to be adsorbed thereby increasing production of high volatile fatty acids to a higher level and its conversion into methane. The high adsorption surface area can be due to the circular shape of the ferrous pebbles 150. The motor 125 is connected to the gearbox 130, the stirrer 135, and the plurality of stirrer blades 140. The motor is connected to an Arduino circuit which operate the motor 140.

A method of enhancing methane generation in biogas production starts with installation to attach the plurality of porous linen pouches 145 onto the plurality of stirrer blades 140 of the semi-continuous stirring tank reactor 100 as shown in FIG. 1.

Cow manure and glucose can be fed into the semi-continuous stirring tank reactor 100 via the feedstock inlet 105. The glucose can be fed continuously to the semi-continuous stirring tank reactor 100 at a rate of 2 grams per liter per day. Incubating the cow manure and glucose inside the semi-continuous stirring tank reactor 100 for a duration of 15 days can form waste activated sludge with methanogen growth. During the incubation period, methanogen growth can be enhanced. The methanogen growth can also be enhanced by surface areas of each of the plurality of ferrous pebbles 140.

After the 15 days, flowing heated water through a water jacket inlet 115 and a water jacket outlet 120 surrounding an exterior of the semi-continuous stirring tank reactor 100 to heat the semi-continuous stirring tank reactor 100 can provide a mesophilic condition. The heated water flowing through the water jacket inlet 115 and water jacket outlet 120 can have a temperature of about 37±1° C. The mesophilic condition can include heating the semi-continuous stirring tank reactor 100 to about 37±1° C.

Rice husk and water can be fed into the semi-continuous stirring tank reactor 100 via the feedstock inlet 105. The rice husk can be fed to the semi-continuous stirring tank reactor 100 at a rate of 5 grams of volatile solid per liter per day. The rice husk can contain volatile solids which are basically those portions of the total mass of the rice husk which can easily be accessible by the methanogen microorganisms and can be converted into methane and other related gases. A pH of the waste activated sludge and the water in the semi-continuous stirring tank reactor 100 can be about 6.9 and about 7 respectively.

The rice husk, the water, and the formed waste activated sludge can be mixed together to form a mixture, wherein an optimum pH of the mixture can be between about 6.5 and about 7.5. If the pH of the mixture in the semi-continuous stirring tank reactor 100 is outside of this optimum range, then the biogas production will be inhibited. The pH was determined at regular 10-day intervals and it was found in the range of about 6.7 to about 7.3. Mixing can be provided by the stirrer blades 140 being rotated automatically at a speed of 360 rpm for 5 minutes every hour for 180 days. A working volume of the semi-continuous stirring tank reactor 100 is very important since it affects the methanogen microorganisms and the volatile solids from the rice husk in the semi-continuous stirring tank reactor 100.

The semi-continuous stirring tank reactor 100 can include two basic portions. The first one is a digestate of feedstock working volume that can include the formed waste activated sludge, the rice husk, and the water. The second portion of the semi-continuous stirring tank reactor 100 can include a gas holder which is about 10% of the total semi-continuous stirring tank reactor 100 volume. In an embodiment, the total volume of the semi-continuous stirring tank reactor 100 can be 12 L, of which 10 L can be the digestate of the feedstock working volume and 2 L can be used for storing produced biogas. A total of the plurality of ferrous pebbles 150 applied to the semi-continuous stirring tank reactor 100 can be 30 g/L and can have a total weight of 300 grams. When the ferrous pebbles 150 are applied at 30 g/L to the semi-continuous stirring tank reactor 100, an adsorption surface area for the methanogen microorganisms can be enhanced.

An embodiment of the present systems and methods can include initiating an anaerobic digestion process during the mixing, wherein the anaerobic digestion process can comprise hydrolysis, acidogenesis, acetogenesis and methanogenesis to produce high volatile fatty acids. The methanogen microorganisms from the waste activated sludge can be reacted with the rice husk to produce the high volatile fatty acids during the acidogenesis and acetogenesis processes. The high volatile fatty acids can be further disintegrated in the methanogenesis process into biogas which contains methane, carbon dioxide and hydrogen. However, hydrogen is relatively unstable and can be converted into methane. Hence, methane can be the main product of these anaerobic digestion steps. The higher volatile fatty acids production during the anaerobic digestion process can be associated with higher methane generation.

Also, in another embodiment, during the acidogenesis and acetogenesis processes, the production of the high volatile fatty acids can be increased to a higher level by enhancing adsorption of the methanogen microorganisms onto the surface areas of each of the plurality of ferrous pebbles 150. As the high volatile fatty acids production increases, a higher level of volatile fatty acids can result and can react with each of the plurality of ferrous pebbles 150, resulting in a reduction environment for the volatile fatty acids which allow more and more volatile fatty acids to be converted into methane while producing biogas through a mechanism of oxidation and electron transfer that break down the volatile fatty acids molecules and stabilize their conversion into methane as shown in Equation 1, below. Ferrous' has a standard hydrogen potential of 0.771 which can promote reduction environments and vacuum for higher volatile fatty acids production. The presence of ferrous oxide can provide enhanced buffering capacity of the anaerobic digestion process, thus facilitating higher volatile fatty acids stabilization and methane production. Unexpectedly, it was discovered that reacting the plurality of ferrous pebbles 150 with the volatile fatty acids during the acidogenesis and acetogenesis processes resulted in the conversion of 82% higher methane generation within the process period of 180 days compared with the same process ran without the plurality of ferrous pebbles 150.

$$Fe^{+2} \rightarrow Fe^{+3} + e^{-} \text{(oxidation)} \quad (1)$$

$$CH_3COO^- + H^+ \xrightarrow{e^-} CH_4 + CO_2 \text{(reduction)} \quad (2)$$

At the end of the process, all the feedstock or digestate, which includes the formed waste activated sludge, the rice husk, and the water, can be removed from the semi-continuous stirring tank reactor 100 via the feedstock outlet 110. The plurality of porous linen pouches 145 can deteriorate, preventing them from being used again. The plurality of ferrous pebbles 150 can be recovered, as they are typically not consumed by the methanogen microorganisms. Thus, the plurality of ferrous pebbles 150 can be used for the next batch of biogas production.

It is to be understood that the method and system for enhancing methane generation in biogas production is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A system for enhancing methane generation in biogas production, the system comprising:
   a semi-continuous stirring tank reactor comprising a feedstock inlet, a feedstock outlet, a water jacket inlet, a water jacket outlet, a motor, a gear box, a stirrer, a plurality of stirrer blades, and a plurality of porous linen pouches having a plurality of ferrous pebbles disposed therein, one of each of the plurality of porous linen pouches attached to one of each of the plurality of stirrer blades;
   the semi-continuous stirring tank reactor configured to receive and incubate cow manure and glucose to form waste activated sludge with methanogen growth;
   the feedstock inlet configured to feed rice husk and water to the semi-continuous stirring tank reactor;
   the feedstock outlet configured to discharge rice husk, water, and waste activated sludge from the semi-continuous stirring tank reactor;
   the water jacket inlet and water jacket outlet configured to accept flowing water to heat the semi-continuous stirring tank reactor to a mesophilic condition;
   the motor is connected to the gearbox, stirrer, and the plurality of stirrer blades; and the motor is connected to an a circuit which operates the motor.

2. The system for enhancing methane generation in biogas production of claim 1, wherein the motor is further configured to automatically rotate the plurality of stirrer blades at a speed of 360 rpm for 5 minutes every hour for 180 days to mix the rice husk, water, and the waste activated sludge together to form a mixture.

3. A system for enhancing methane generation in biogas production of claim 1, wherein the plurality of stirrer blades comprises 6 stirrer blades and the plurality of porous linen pouches comprises 6 porous linen pouches, the plurality of ferrous pebbles comprises 72 total ferrous pebbles having a total exposed surface area of 241.63 $cm^2$, and a dimension of each of the plurality of ferrous pebbles comprises a diameter of 9.5 mm and a height of 6.5 mm.

4. A system for enhancing methane generation in biogas production of claim 1, wherein each of the plurality of ferrous pebbles in each of the plurality of porous linen pouches comprises 12 ferrous pebbles.

5. A method of enhancing methane generation in biogas production, the method comprising:
   installing a plurality of porous linen pouches onto a plurality of stirrer blades of a semi-continuous stirring tank reactor, wherein each of the plurality of porous linen pouches comprise a plurality of ferrous pebbles;
   feeding cow manure and glucose into the semi-continuous stirring tank reactor via a feedstock inlet;
   incubating the cow manure and glucose inside the semi-continuous stirring tank reactor for a duration of time to form waste activated sludge with methanogen growth, wherein the methanogen growth is enhanced by surface areas of each of the plurality of ferrous pebbles;
   flowing heated water through a water jacket inlet and a water jacket outlet surrounding an exterior of the semi-continuous stirring tank reactor to heat the semi-continuous stirring tank reactor to provide a mesophilic condition;
   feeding rice husk and water into the semi-continuous stirring tank reactor via the feedstock inlet,
   mixing the rice husk, the water, and the formed waste activated sludge together to form a mixture, wherein a pH of the mixture is between about 6.5 and about 7.5;
   initiating an anaerobic digestion process during the mixing, wherein the anaerobic digestion process comprises hydrolysis, acidogenesis, acetogenesis and methanogenesis to produce high volatile fatty acids;
   increasing the production of the high volatile fatty acids to a higher level by enhancing adsorption of the methanogen microorganisms onto the surface areas of each of the plurality of ferrous pebbles; and
   reacting the higher level of the high volatile fatty acids with each of the plurality of ferrous pebbles to increase conversion of the higher level of volatile fatty acids to methane while producing biogas.

6. The method of enhancing methane generation in biogas production of claim 5, wherein each of the plurality of ferrous pebbles are stitched within a respective one of each of the plurality of porous linen pouches and each of the plurality of ferrous pebbles have a circular shape.

7. The method of enhancing methane generation in biogas production of claim 5, wherein the plurality of stirrer blades comprises 6 stirrer blades and the plurality of porous linen pouches comprises 6 porous linen pouches.

8. The method of enhancing methane generation in biogas production of claim 5, wherein each of the plurality of ferrous pebbles in each of the plurality of porous linen pouches comprises 12 ferrous pebbles.

9. The method of enhancing methane generation in biogas production of claim 5, wherein one of each of the plurality of porous linen pouches are installed on one of each of the plurality of stirrer blades.

10. The method of enhancing methane generation in biogas production of claim 5, wherein the plurality of ferrous pebbles comprises 72 total ferrous pebbles having a total exposed surface area of 241.63 cm$^2$, and a dimension of each of the plurality of ferrous pebbles comprises a diameter of 9.5 mm and a height of 6.5 mm.

11. The method of enhancing methane generation in biogas production of claim 5, wherein a total volume of the waste activated sludge, rice husk, and water within the semi-continuous stirring tank reactor is 10 L and a total weight of the plurality of ferrous pebbles is 300 grams.

12. The method of enhancing methane generation in biogas production of claim 5, wherein a total of the plurality of ferrous pebbles applied to the CSTR is 30 g/L.

13. The method of enhancing methane generation in biogas production of claim 5, wherein the glucose is fed continuously to the semi-continuous stirring tank reactor at a rate of 2 grams per liter per day.

14. The method of enhancing methane generation in biogas production of claim 5, wherein the duration of time is 15 days.

15. The method of enhancing methane generation in biogas production of claim 5, wherein the rice husk is fed to the semi-continuous stirring tank reactor at a rate of 5 grams of volatile solid per liter per day.

16. The method of enhancing methane generation in biogas production of claim 5, wherein a pH of the waste activated sludge and the water in the semi-continuous stirring tank reactor are about 6.9 and about 7 respectively.

17. The method of enhancing methane generation in biogas production of claim 5, wherein the mesophilic condition comprises heating the semi-continuous stirring tank reactor to about 37±1° C.

18. The method of enhancing methane generation in biogas production of claim 5, wherein the heated water flowing through the water jacket inlet and water jacket outlet has a temperature of about 37±1° C.

19. The method of enhancing methane generation in biogas production of claim 5, wherein the mixing is provided by the stirrer blades being rotated automatically at a speed of 360 rpm for 5 minutes every hour for 180 days.

20. The method of enhancing methane generation in biogas production of claim 5, wherein the methanogen microorganisms from the waste activated sludge are reacted with the rice husk to produce the high volatile fatty acids during the acidogenesis and acetogenesis processes.

* * * * *